United States Patent [19]

Arpe

[11] 3,972,949

[45] Aug. 3, 1976

[54] PROCESS FOR PREPARING GLYCOL DIMETHYL ETHERS

[75] Inventor: Hans-Jürgen Arpe, Fischbach, Taunus, Germany

[73] Assignee: Hoechst Aktiengesellschaft, Frankfurt am Main, Germany

[22] Filed: July 14, 1975

[21] Appl. No.: 595,732

[30] Foreign Application Priority Data

July 16, 1974 Germany............................ 2434057

[52] U.S. Cl. ........................ 260/615 R; 260/615 B; 252/454; 252/455 R; 252/459
[51] Int. Cl.$^2$......................................... C07C 41/00
[58] Field of Search ..................... 260/615 R, 615 B

[56] References Cited

UNITED STATES PATENTS 2,397,514  4/1946  Stalt............................... 260/615 R Primary Examiner—Howard T. Mars
Attorney, Agent, or Firm—Curtis, Morris & Safford

[57] ABSTRACT

Glycol dimethyl ethers of the formula $CH_3O(CH_2CH_2O)_nCH_3$, wherein $n$ is an integer of from 1 to 8 are prepared by reacting the corresponding glycol monomethyl ether formal with hydrogen under a pressure of 30 to 300 bars and at a temperature of 50° to 250°C in the presence of catalysts comprising silicon dioxide and aluminium oxide or oxides of rare earths or mixtures thereof and containing additionally nickel, cobalt and copper.

3 Claims, No Drawings

PROCESS FOR PREPARING GLYCOL DIMETHYL ETHERS

The present invention provides a catalytic process for preparing glycol dimethyl ethers of the formula $CH_3O(CH_2CH_2O)_nCH_3$, wherein $n$ is an integer from 1 to 8, using as starting product the corresponding glycol monomethyl ethers of the formula $CH_3(CH_2CH_2O)_nH$. In this process the formals $[CH_3O(CH_2CH_2O)_n]_2CH_2$ of the glycol monomethyl ethers are submitted to a hydrogenolytic cleavage. Glycol dimethyl ethers are valuable solvents or are used as extracting agents, absorbents or gas-purifying agents, for example, in the elimination of acidic components such as $CO_2$, $SO_2$ or $H_2S$ from refinery or natural gases. The dimethyl ethers for this purpose are used separately or in form of mixtures. A frequently used product in the gas purification process, for example, has the composition according to the aforesaid formula wherein $n$ mainly is an integer of from 4 to 7.

The corresponding monomethyl ethers are especially convenient for an economical technical preparation of the dimethyl ethers of the glycols, as they may be readily obtained from the chemicals ethylene oxide and methanol produced on a large scale.

There are known a series of processes converting monomethyl ethers of the glycols into their dimethyl ethers. According to German Pat. No. 1,295,833 and U.S. Pat. No. 3,591,641 the monomethyl ether firstly is reacted with sodium metal to give the sodium glycolate while forming $H_2$ and the glycolate obtained is converted into the dimethyl ether with methyl halides, preferably methyl chloride, while precipitating sodium halide. This process, as similar processes, has the drawback of a complete loss of chlorine and sodium and of a high waste water charge.

A further process uses dimethyl sulfate for reacting sodium glycolate of the monomethyl ether. In this case mineral byproducts also considerably charge the waste water.

The present invention provides a process for preparing glycol dimethyl ethers of the formula $CH_3O(CH_2CH_2O)_nCH_3$ wherein $n$ is an integer of from 1 to 8, from the formals of the corresponding glycol monomethyl ethers, which comprise reacting the formals with hydrogen under a pressure of from 30 to 300 bars at a temperature of 50° to 250°C in the presence of catalysts comprising silicon dioxide and moreover aluminium oxide or oxides or rare earth metals or the aforesaid three components and containing additionally the metals nickel, cobalt or copper.

The formals of the glycol monomethyl ethers may be readily prepared by reacting them with substances yielding formaldehydes such as para-formaldehyde or trioxane, for example, according to German Auslegeshcrift No. 1,293,143. They may likewise be prepared in an especially economic manner from aqueous formaldehyde solutions.

The total reaction, consequently, is characterised by the equations I and II:

I (formation of formal):

$$2\ CH_3O(CH_2CH_2O)_nH + HCHO \rightarrow [CH_3O(CH_2CH_2O)_n]_2CH_2 + H_2O$$

II (hydrogenolysis of formal):

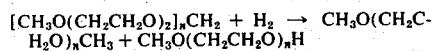

As one mole of formal is cleaved by $H_2$ into one mole of glycol dimethyl ether and one mole of glycol monomethyl ether, i.e. the substance used as starting material for the reaction according to equation I, the following summation equation III may be set up:

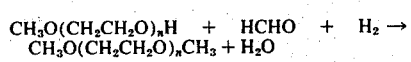

Equation III demonstrates the economical advantage of the process of the invention compared to the processes hitherto used. The only by-product obtained is water.

If mixtures of glycol monoethers are used for preparing the formals according to equation I it must be considered that there are formed not only symmetric formals but also unsymmetric formals of the formula $CH_3O(CH_2CH_2O)_nCH_2(OCH_2CH_2)_mOCH_3$ wherein $n$ and $m$ are different. These unsymmetric formals may also be hydrogenolized according to equation II.

The hydrogenolysis of acetals i.e. the cleavage of acetals by molecular hydrogen or by metallo-organic reducing agents yielding hydrogen principally is a reaction known for a long time.

The examples in monographs such as for example R. L. Augustine, Catalytic Hydrogenation, New York, 1965; M. Freifelder, Practical Catalytic Hydrogenation, New York, 1965; M. Freifelder, Practical Catalytic Hydrogenation, New York 1971; F. Zymalkowski, Katalytische Hydrierungen, Stuttgart, 1965 or also in German Pat. Nos. 888,999 and 911,849 show that formals are generally used which are prepared from aromatic aldehydes or from aliphatic aldehydes of at least 3 carbon atoms by reacting them with alcohols.

It was therefore surprising that acetals resulting from the reaction of alcohols with formaldehyde, i.e. formals, may be used successfully in the hydrogenolysis, as the formation of an ether in the hydrogenolysis should be realized via a vinyl ether primarily formed which may only be obtained from an acetal of an aldehyde of at least 2 carbon atoms, according to R. L. Augustine cited above and other authors.

The selectivities of dimethyl glycol ethers are however unsatisfactory when operating in the presence of the nickel catalysts hitherto used for the aforesaid hydrogenolysis (cf. comparative examples).

The hydrogenation activity of such nickel catalysts generally activated by bases such as for example Raney nickel activated by $Al(OH)_3$ or further commercially available nickel catalysts by manganium, magnesium, aluminium or chromium oxides is such that both C—O bondings of the formal are hydrogenolized. A complete cleavage of the formal occurs with formation of the monomethyl ether used in the preparation of the formal and smaller quantities of cleavage products. Attempts to reduce the activity of the nickel catalyst activated by bases by the addition of mineral or carboxylic acids in order to obtain a greater selectivity lead to the formation of dimethyl glycol ethers having, however, a small and, consequently, economically unsatisfactory selectivity. The presence of mineral or carboxylic acids in the reaction medium moreover leads to the formation of soluble nickel salts causing a reduction of the life time of the catalysts.

It was surprising that a controlled reduction of the activity of the catalyst of the invention could be obtained by using a special acidic support such that the hydrogenolysis of the formals of glycol monomethyl ethers could be effected with an optimal selcetivity and activity and, consequently, in a very economical manner.

Three methods at least may be used principally for preparing the catalyst according to the invention:

In the first two methods firstly is prepared the oxide mixture of silicium with aluminium and/or the rare earth metals and the support thus obtained is impregnated thereafter with the metals nickel, cobalt or copper.

In the third method the combination of the elements according to the invention may be obtained in one step, however, in a preliminary stage to their final active form as oxides on one hand and as metals on the other hand.

According to the first method a $SiO_2$ support in the form of kieselguhr or silica gel is prepared having a content of 1 to 20% by weight, calculated on the support, of $Al_2O_3$ and/or rare earth oxides. Rare earths (lanthanides) are the elements of the periodic number 58 to 71, i.e. those reaching from cerium to lutetium inclusively.

The $SiO_2$ support may be impregnated in usual manner, for example, with aqueous solutions of mineral or organic salts of aluminium and/or the rare earths.

The rare earth oxides may be used separately as for example cerium oxide or as mixtures commercially available as didymium oxides, for example, composed of cerium, praseodymium, neodymium and small quantities of samarium, gadolinium, ytterbium etc.

The salts are then converted in known manner, for example, with aqueous ammonia into the oxides or oxide hydrates.

In the second method for preparing the oxide mixtures silicon dioxide and the hydroxides or the oxide hydrates of aluminium and/or the rare earths are precipitated simultaneously. For this purpose aqueous solutions of aluminium nitrate or of rare earth chlorides, for example, are added to aqueous alkaline solutions of alkali silicate, for example, in the form of sodium silicate and the pH is adjusted to a value of about 7 to 8, namely with alkali hydroxides or carbonates if the solution is acid or with acids such as nitric acid or hydrochloric acid if the solution is basic. The weight proportion of aluminium or the rare earths and silicon is not critical. It generally is in the range of 3 to 50% by weight of $Al_2O_3$ or $Di_2O_3$ (where Di stands for any member of the group of rare earths) calculated on the total weight of $Al_2O_3$ and $SiO_2$ of of $Di_2O_3$ and $SiO_2$, without limiting however the possible range of the components of the mixture.

For obtaining an especially active and selective catalyst of the composition according to the invention it has proved particularly advantageous, as regards the preparation of the support according to method 1 (ready-made $SiO_2$ support) or method 2 (simultaneous precipitation), to carry out a calcination of the support in a determined temperature range after having converted the designed salts of the metals into the hydroxides or oxide hydrates.

The calcination of the oxide mixture may be carried out by heating it to temperatures of 150° to 850°C, preferably of 500° and 700°C. The time of calcination is not critical. It may be in the range of 1 to 30 hours, preferably of from 3 to 20 hours. After this preliminary treatment the oxides may still be present partially in their original form or they may have reacted to give silicious structures or silicates having acid properties.

For preparing the hydrogenolysis catalyst nickel, cobalt or copper are applied to the aforesaid support in conventional manner.

The metals are formed on the support in a finely dispersed form from their compounds such as oxides, hydroxides, carbonates, nitrates, acetates, oxalates or other organic compounds or complexes by reduction with gases having a reducing effect such as $H_2$ or CO or with vapors wuch as methanol or ethanol.

For this purpose the support is impregnated with a solution of the afore-said nickel, cobalt or copper compounds such as for example an aqueous solution of the nitrates and reduced. It is likewise possible to convert the compounds firstly into the hydroxides prior to reducing them by adding the impregnated carrier material into aqueous alkaline solution or into aqueous $NH_3$ solution. After having washed out foreign ions the hydroxides are reduced to metals in similar manner as described above. The reduction temperature generally is in the range of 200° to 600°C, preferably of 300° to 500°C.

The concentration of the nickel, cobalt or copper on the support may vary within wide limits. Concentrations in the range of 1 to 30% by weight calculated on the support lead to a very good activity. It is also possible to operate with concentrations above 30% by weight.

The third method for preparing the catalyst is used preferably. It consists in preparing by one precipitation the combination of the elements according to the invention, having not yet primarily its catalytically efficient form, however.

It may be carried out in the following manner:

The aforesaid salts of the "hydrogenation component", i.e. nickel, cobalt or copper are introduced while stirring into the alkali silicate solution together with the water soluble salts of aluminium and/or the rare earth metals. The pH may be adjusted to a value of about 7 to 8 as described above.

The concentration proportions of nickel, cobalt and copper calculated on the total weight of the oxides of silicon, aluminium and/or the rare earths for a "precipitation catalyst" prepared in this way are not critical. The hydrogenation component may be present in a considerably higher concentration compared to the first two methods for preparing the catalyst. A concentration range of 10 to 80% by weight, preferably of 40 to 7% by weight is possible.

In contrast to the "impregnation catalyst" (according to method 1 or 2) the calcination of the oxides of silicon, aluminuium and/or the rare earths is only carried out after reduction of the metal hydroxides in order to avoid a possible silicate or spinel formation. This means that reduction is carried out with gases having a reducing effect or with dissolved reducing agents such as hydrazine hydrate, the reduction product is dried and calcinated at temperatures of 150° to 850°C preferably of 500° and 700°C for a period of 1 to 30 hours, preferably of 3 to 20 hours.

The hydrogenolysis in the process according to the invention is carried out at temperatures of 50° to 250°C and under a hydrogen pressure of 30 to 300 bars. A satisfactory activity and selectivity may also be obtained when operating under conditions outside of the said limits.

The formals of the monomethyl ethers of mono-, di- etc. up to octaethylene glycol or of any mixtures of these products are reacted with hydrogen in pressure apparatus for cleaving them by hydrogenolysis. It may be worked discontinuously thereby, for example, in an autoclave containing a finely dispersed moved catalyst. Cleavage by hydrogenolysis may also be carried out continuously in pressure reactors, in the vapor or trickling phase generally in the presence of a fixed catalyst. Further common embodiments of such a hydrogenation with heterogeneous catalysts are also convenient. The formals may be charged in pure undiluted form or diluted with a solvent, for example with alcohols such as methanol or ethers or even with the reaction products, i.e. mono- or dimethyl ethers of the corresponding glycol (cf. reaction equation II).

After absorption of the calculated quantity of hydrogen in the autoclave or after passage of the reaction product through the reactor, the pressure is released and the reaction products are separated by distillation.

When operating without solvents or with the reaction products are solvents the reaction mixture may be worked up in especially simple manner. When using a single formal the gylcol dimethyl ether in all cases is the product of the lowest boiling point, which may be separated by film evaporation. Unreacted formal and the glycol monomethyl ether are recycled to the reaction process with a solution or substance yielding formaldehyde.

When using mixtures of the formals of different glycol monomethyl ethers it may be advantageous to convert after hydrogenolysis the monomethyl ethers necessarily obtained besides the dimethyl ethers (cf. equation II, page 2) into the formals and to separate the dimethyl ethers subsequently from the high boiling formals by distillation in a purer form. By this method the intervals between the boiling point range of the components of the reaction mixture are extended.

The diethers, consequently, may be obtained in an economic and simple manner by the process according to the invention using the easily obtainable monoethers of the glycols.

The parameters in the following examples for the formals used and the mono- and dimethyl ethers obtained therefrom are defined as follows:

The conversion of a formal is defined as the molar proportion in percent of the converted formal calculated on the formal charged.

The selectivity of the mono- or dimethyl ether is its molar proportion in percent in the reaction product calculated on the formal converted. Owing to the stoichiometry of the reaction equation II the selectivity of both mono- and dimethyl ethers may be 100% by mole each by mole optimally. In case of an unselective cleavage of the formal yielding monomethyl ethers above the stoichiometric amount the selectivity of monomethyl ethers consequently may be greater than 100%. The yield of dimethyl ethers is its molar proportion in percent calculated on the formal charged.

The following examples illustrate the invention:

EXAMPLES

Comparative Example 1

200 g of the formal of the glycol monomethyl ether —$(CH_3OCH_2CH_2O)_2CH_2$ were reacted with hydrogen in a 1 liter autoclave provided with a magnetic type lifting stirrer in the presence of 10 g of a commercial nickel catalyst with 55% by weight of nickel on a $SiO_2$ support activated with magnesium oxide and in the presence of 10 g of acetic acid at 145°C and under an initial pressure of 100 bars (initial pressure is the hydrogen pressure at a temperature of 15° to 25°C. Stirring was interrupted after a reaction time of three hours and the autoclave was cooled. The green coloured reaction product was liberated from the catalyst by filtration and analyzed by a gas chromatography. With a conversion of the formal of 64% by mole a selectivity of the monomethyl ether of 66% by mole and of the dimethyl ethers of 60% by mole was obtained.

When using instead of the Ni—MgO—$SiO_2$ catalyst Raney nickel activated by aluminium hydroxide in the same concentration with acetic acid, a hydrogen absorption could not been observed at a hydrogen initial pressure of 100 bars np to a temperature of 160°C, i.e. a hydrogenolysis of the formal of the glycol monomethyl ether did not take place.

Comparative Example 2

When adding under identical conditions as in comparative example 1 instead of 10 g of acetic acid 10 g of phosphoric acid to the Ni—MgO—$SiO_2$ catalyst a conversion of formal of 95% by mole could be obtained after a reaction time of 3 hours at a temperature of maximally 152°C. The selectivity of dimethyl ether and of monomethyl ether was in the range of 69% of or 127% by mole, i.e. the selectivity with regard to the monomethyl ether exceeding the theoretical selectivity points to the unselective hydrogenolysis of the diether.

EXAMPLE 1

11.32 g of $AlCl_3 \cdot 6 H_2O$ were dissolved in 52 ml of $H_2O$ and 150 ml of a silica gel (58.1 g) of a granular size of 0.5 to 1.5 mm and a surface of 300 m²/g were impregnated therewith. After drying at 140°C and under a pressure of about 270 mbars the impregnated $SiO_2$ was introduced by stirring into a solution of 22 ml of a 25% aqueous solution of $NH_3$ and 150 ml of $H_2O$, filtered off and washed with water until all chlorine ions had been removed. The $SiO_2$ impregnanted with Al-$(OH)_3$ was again dried at 140°C and under a pressure of about 270 mbars and calcinated subsequently for 15 hours at 600°C. 45 ml of the $Al_2O_3/SiO_2$ support were impregnated with a solution of 17.93 g of $Ni(NO_3)_2 \cdot 6 H_2O$, submitted to a preliminary drying on a vapor bath, further dried at 140°C and under a pressure of 270 mbars and reduced with hydrogen for 2 hours at 250°C and for 2 hours at 400°C.

14.2 g of the $Ni/Al_2O_3/SiO_2$ catalyst thus obtained were moistened with a small quantity of formal of methyl glycol at the exclusion of air and ground to fine particles. The catalyst was then introduced with 200 g of the formal of the methyl glykol —$(CH_3OCH_2C-H_2O)_2CH_2$— into a 1 liter autoclave provided with a magnetic type lifting stirrer and the mixture was hydrogenized under an initial hydrogen pressure of 100 bars for 3 hours at a maximal temperature of 155°C. The theoretically expected hydrogen absorption was terminated then. After expansion and filtering off of the catalyst which may be anew used in the hydrogenolysis a colourless clear reaction product was obtained. The formal had been converted quantitatively to the dimethyl and monomethyl ether with practically 100% by mole selectivity each, i.e. the yield of dimethyl glycol was nearly 100% by mole. The dimethyl glycol having a boiling point from 82° to 83°C could be separated in a simple distillation apparatus from monoethyl glycol having a boiling point of from 137° to 138°C. The monomethyl ether was recycled to the formal preparation apparatus.

EXAMPLE 2

1500 g of $Ni(NO_3)_2 \cdot 6 H_2O$ and 370 g of $Al(NO_3)_3 \cdot 9 H_2O$ were dissolved in 900 ml of $H_2O$ and introduced while stirring into a solution of 500 g of sodium silicate (consisting of about 25 to 30% by weight of $SiO_2$) and 600 g of $Na_2CO_3$ in 1700 ml of $H_2O$ heated to 70° to 90°C within 2 hours. The pH of the reaction mixture was about 7. The precipitate was filtered off with suction and washed with water until it was free from nitrate ions. After drying at 140°C and under a pressure of about 300 mbars this preliminary catalyst was reduced with hydrogen for 9 hours at 400°C and calcinated in a slight hydrogen current for 9 hours at 600°C.

The $Ni-Al_2O_3-SiO_2$ catalyst obtained was moistened in a nitrogen atmosphere with a small quantity of formal of monomethyl glycol and ground to fine particles. Thereafter it was introduced with 15 kg of the formal of the monomethyl glycol, i.e. $(CH_3OCH_2CH_2O)_2CH_2$ in a 25 liter autoclave provided with a magnetic type lifting stirrer and the hydrogenation was carried out under an initial hydrogen pressure of 100 bars and at a maximal temperature of 160°C. After having repeatedly replaced the consumed hydrogen the hydrogenated solution was withdrawn from the autoclave and worked up by distillation. The conversion of the formal practically was complete. 7.34 kg of dimethyl glycol corresponding to a yield of 89.2% by mole were obtained.

EXAMPLE 3

An $Al_2O_3/SiO_2$ support was prepared in an analogous manner to example 1 and 62 g thereof were impregnated with a solution of 23.5 g of $Cu(NO_3)_2 \cdot 3 H_2O$ in 48 ml of $H_2O$. After drying and reducing with hydrogen 14.4 g of the impregnated support were reacted for 3 hours with 200 g of $(CH_3OCH_2CH_2O)_2CH_2$ in a 1 liter autoclave provided with a magnetic type lifting stirrer at maximally 180°C and under a hydrogen pressure of 110 bars. With a conversion of 43.1% by mole selectivities of dimethyl ether of 95% or of monoethyl ether of 91% were obtained. After distilling off the dimethyl glycol the mixture of methyl glycol and unconverted formal of the methyl glycol was recycled to the reaction with formaldehyde yielding the formal.

EXAMPLE 4

Instead of impregnating a silica gel with an aluminium salt 100 ml of $SiO_2$ (surface 160 m²/g, pore volume 0.8 ml/g) were impregnated in an analogous manner to example 1 with a solution of 5.25 g of $Di_2O_3$ (a commercial product, consisting of a mixture of the oxides of cerium, praseodymium, neodymium and small quantities of samarium, gadolinium, ytterbium etc.) in 38 ml of glacial acetic acid, dried and calcinated for 15 hours at 600°C.

This $Di_2O_3/SiO_2$ support was impregnated with an aqueous solution of 30.6 g of $Cu(NO_3)_2 \cdot 6 H_2O$, dried and reduced with hydrogen.

15.5 g of the $Cu-Di_2O_3/SiO_2$ catalyst were ground to fine particles in 0.805 mole of formal of methyl diglycol —$(CH_3OCH_2CH_2OCH_2CH_2O)_2CH_2$— and hydrogenolized in a 1 liter autoclave provided with a magnetic type lifting stirrer with $H_2$ of an initial pressure of 100 bars at a maximal reaction temperature of 158°C. The hydrogen absorption was terminated after 3 hours. With a conversion of the formal of 76% by mole selectivities of 89 or of 92% by mole of monomethyl or dimethyl ether respectively were obtained.

EXAMPLE 5

100 ml of a commercial aluminum silicate support having a content of 13% by weight of $Al_2O_3$ (surface 95 m²/g, pore volume 0.47 ml/g) were impregnated with a solution of 30.6 g of $Ni(NO_3)_2 \cdot 6 H_2O$ in 20 ml of $H_2O$, dried and reduced with hydrogen for 2 hours at a temperature of 250°C and for 2 hours at a temperature of 400°C.

200 g of formal of the methyl triglycol —$[CH_3O(CH_2CH_2O)_3]_2CH_2$ — were hydrogenized for 5 hours with 14.4 g of the $Ni-Al_2O_3/SiO_2$ catalyst previously prepared in a 1 liter autoclave provided with a magnetic type lifting stirrer under a initial hydrogen pressure of 100 bars at a temperature of from 155° to 160°C. After cooling and filtering off the catalyst 97 g of dimethyl triglycol of the formula —$CH_3O(CH_2CH_2O)_3CH_3$ — could be isolated by distillation corresponding to a yield of 91% by mole.

EXAMPLE 6

600 g of a mixture of formals of the following ethylene glycol mono-methyl ethers:
  9.0% by weight of triethylene glycol monomethyl ether
  24.2% by weight of tetraethylene glycol monomethyl ether
  28.8% by weight of pentaethylene glycol monomethyl ether
  20.8% by weight of hexaethylene glycol monomethyl ether
  10.8% by weight of heptaethylene glycol monomethyl ether
  4.7% by weight of octaethylene glycol monomethyl ether
  1.7% by weight of higher ethylene glycol monomethyl ether were hydrogenized with 36.5 g of the $Ni-Al_2O_3/SiO_2$ catalyst prepared and composed as in example 4 at a maximal temperature of 158°C for 7 hours and under an initial hydrogen pressure of 100 bars. After cooling and filtering off the catalyst the dimethyl ethers of the glycols formed were distilled off from one moiety of the reaction product until a boiling temperature of 160°C and a pressure of 0.6 to 1 mbars were obtained. 150 g were obtained having a proportion of about 22% by weight of monomethyl ethers. In the second moiety of the reaction product the monomethyl ethers formed in the hydrogenolysis firstly were converted into the corresponding formals by conventional methods and the dimethyl ethers were distilled off from the higher boiling formals of the monomethyl ethers by distillation until a temperature of about 160° to 170°C and a pressure of 0.6 to 1 mbar were reached. 138 g of a mixture of dimethyl ethers could be obtained thus being free from monomethyl ethers.

What is claimed is:

1. Process for preparing glycol dimethyl ethers of the formula $CH_3O(CH_2CH_2O)_nCH_3$, wherein $n$ is an integer from 1 to 8, from a formal of the corresponding glycol monomethyl ethers, which comprises reacting the formals with hydrogen under a pressure of 30 to 300 bars and at a temperature of 50° to 250°C in the presence of a catalyst comprising silicon dioxide and either aluminum oxide or an oxide of a rare earth or a combination of the aforesaid three components and containing additionally the metals nickel, cobalt or copper.

2. Process as claimed in claim 1, which comprises preparing the catalyst by precipitation of the hydroxides or oxide hydrates of all components from aqueous salt solutions at a pH of about 7 to 8, subsequent reduction with hydrogen at a temperature of 200° to 600°C followed by calcination for 3 to 20 hours at a temperature of 500° to 700°C.

3. Process as claimed in claim 1, which comprises, when using a mixture of the formals of different glycol monomethyl ethers, after the hydrogenolysis of said mixtures, firstly reacting the monomethyl ethers formed as by-products in said hydrogenolysis with formaldehyde, paraformaldehyde or trioxane into the corresponding formals and then separating the dimethyl ethers formed in the hydrogenolysis from the reaction mixture by distillation.

* * * * *